United States Patent [19]
Campbell et al.

[11] Patent Number: 5,816,704
[45] Date of Patent: Oct. 6, 1998

[54] WATER ACTIVITY AND DEW POINT TEMPERATURE MEASURING APPARATUS AND METHOD

[75] Inventors: Gaylon S. Campbell, Pullman, Wash.; David P. Lewis, Princeton, Id.

[73] Assignee: Decagon Devices, Inc., Pullman, Wash.

[21] Appl. No.: 659,200

[22] Filed: Jun. 4, 1996

[51] Int. Cl.$^6$ .................................................. G01N 25/68
[52] U.S. Cl. .............................................. 374/28; 374/16
[58] Field of Search ................................. 374/18, 16, 20, 374/27, 28, 47, 135, 138, 208; 73/29.01

[56] References Cited

U.S. PATENT DOCUMENTS

| | | | |
|---|---|---|---|
| 3,142,986 | 8/1964 | Wood et al. | 374/18 |
| 4,579,462 | 4/1986 | Rall et al. | 374/28 |
| 5,302,026 | 4/1994 | Phillips | 374/135 |
| 5,507,175 | 4/1996 | Cooper | 374/20 |

FOREIGN PATENT DOCUMENTS

| | | | |
|---|---|---|---|
| 1128606 | 1/1957 | France | 374/28 |
| 26 34 274 | 2/1978 | Germany | 374/28 |
| 1659818 | 6/1991 | U.S.S.R. | 374/28 |

*Primary Examiner*—G. Bradley Bennett
*Attorney, Agent, or Firm*—Foster & Foster

[57] ABSTRACT

A dew point temperature measuring apparatus and method, which may be used to determine water activity, includes a chamber in which a sample of air is measured, an air circulation device positioned within the chamber, a sensor to measure the sample temperature, a relative humidity sensor, and a diverter for causing air circulating within the chamber to directly impinge the relative humidity sensor. Another embodiment involves mounting an air circulation device within the chamber such that it forces air inside the chamber to impinge directly upon the relative humidity sensor to reduce boundary layer resistance. Still another embodiment of the invention involves utilizing a temperature control device to control the temperature of interior surfaces within the chamber at a temperature higher than the sample of air within the chamber. Yet another embodiment of the present invention involves a product relative humidity sensor in which a dew point temperature sensor, such as a resistive or capacitive sensor, is used in combination with a heater and/or a fan to speed the time required to reach equilibrium and the accuracy of dew point temperature measurements.

35 Claims, 6 Drawing Sheets

WATER ACTIVITY AND DEW POINT TEMPERATURE MEASURING APPARATUS AND METHOD

TECHNICAL FIELD

This invention relates to measuring devices, and more specifically, to devices used to measure dew point temperature in air and water activity in samples.

BACKGROUND OF THE INVENTION

There are numerous practical applications for measuring the dew point temperature of a sample of air. For example, dew point temperature is used to measure water activity in any number of product samples. In addition, the dew point temperature of air can be used to measure the relative humidity of ambient air in any given environment.

Water activity measurements can serve several useful purposes. Water activity may be measured in plants, soils, and foods, as well as other product samples. Most commonly, water activity is measured with respect to food products. Water activity or water potential is measured in food products to determine or predict food stability with respect to physical properties, rates of deteriorative reactions, and microbial growth. Water activity is a primary factor that determines shelf-life of food products. Several other factors, such as temperature and pH, can influence whether organisms will grow in food products, as well as the rate at which such organisms will grow. Nonetheless, water activity may be the most important factor in determining whether organisms will grow in food products.

Water activity is defined as the ratio of water vapor pressure over a product sample, such as food, to that over pure water. A multiplication of water activity by 100 gives the relative humidity of the atmosphere in equilibrium with the product sample being measured. Most bacteria, for example, will not grow at water activities below 0.91, and most molds do not grow at water activities below 0.80. By measuring the water activity of food products, it is possible to predict which micro-organisms will and will not be potential sources of spoilage. Water activity is not the same as water content.

There are a number of traditional ways to reduce water activity in a food product. Such methods include cooking, baking, and dehydrating, all of which drive off water. Another method involves diluting the water by adding solutes, typically sugars or sodium chloride, or by adding humectants to bind the water. This creates an imbalance in osmotic pressure which draws the water from cells. Food designers face significant challenges in maintaining sufficiently low water activity with many of today's fat replacers.

Reducing the water activity also minimizes undesirable chemical changes occurring in foods during storage. The processes used to reduce the water activity in goods include concentrating, dehydrating, and freeze-drying. Freezing can also control food spoilage. Freezing turns water into ice crystals and makes water unavailable to micro-organisms or for reactions with food components. Measurements of water activity or water potential are typically done by enclosing samples in sealed chambers and measuring the humidity in the chamber at equilibrium. The accuracy of these measurements is strongly influenced by temperature. A 1° C. error in measuring the difference between the sample and the sensor temperatures results in a possible measurement error of 0.06 (i.e., 6% humidity), much larger than the total range of measurements in high moisture applications. Temperature differences must be known to within approximately 0.001° C. for acceptable accuracy in some high humidity applications. Because of the extreme precision required in temperature measurement and control, it has traditionally been assumed that the chambers in which water activity is measured need to be isothermal for accurate measurement. Extensive efforts have gone into designing systems which are isothermal. Some early systems used precise constant temperature baths. Later versions have used massive chambers made from high thermal conductivity materials to try to create isothermal conditions in the measurement chamber.

A significant problem for high humidity applications with respect to traditional systems for measuring relative humidity and water activity relates to the adsorption of water vapor on the walls of the chamber in which measurements are taken. With no vapor adsorption, equilibrium would occur within a matter of seconds. In practice, however, reaching equilibrium can take hours, depending on the material from which the chamber is constructed. In some types of chambers, large quantities of water are adsorbed. The quantity of water being adsorbed will increase as the chamber humidity approaches 1.0 (i.e., 100% humidity). Thus, equilibrium of very wet (i.e., high humidity) samples has traditionally required significant amounts of time.

One of the standard methods of measuring water activity is through the use of a capacitive sensor. The capacitance sensor is used where the water activity of a food sample can be determined from the relative humidity of the air surrounding the sample when the two are at equilibrium. The sample must be in an enclosed space. Thereafter, the sample and the water vapor in the air need time to come to equilibrium. At that point in time, the water activity of the sample and the relative humidity of the air are equal. A capacitive sensor involves a sensor made from a hygroscopic polymer and associated circuitry that gives a signal relative to the equilibrium relative humidity. The sensor measures the equilibrium relative humidity of the air immediately around it. A potential drawback of this method is that the equilibrium relative humidity is equal to the sample water activity only so long as the temperatures of the sample and the sensor are the same. Capacitive sensors require between thirty and ninety minutes before the food sample and the air surrounding the food sample reach equilibrium with respect to temperature and vapor.

A standard method for measuring the vapor pressure of air, either for determining, atmospheric moisture or water activity of foods and other materials, is to use a chilled-mirror sensor which involves cooling a mirror or other reflective surface until dew forms on the surface. The temperature at which dew forms is taken as the dew point temperature. The dew point temperature is defined as the temperature at which liquid water and water vapor are at equilibrium. The measurement of dew point temperature is therefore commonly assumed to be an equilibrium measurement. Such dew point measurements cannot, however, be equilibrium measurements because the reflective surface must cool below the dew point temperature before any dew will form on it. The overcooling required for dew to form constitutes an error in the measurement of the dew point temperature. The magnitude of the error can be assessed through an analysis of the cooling and dew forming process.

Assume that an amount of condensation, $W(g/m^2)$ is required to register the dew point. If $E(gm^{-2}s^{-1})$ is the rate of condensation, then $$W = \int_o^t E\,dt \quad (1)$$

The rate of condensation can be computed from $$E = \frac{\rho_{vs} - \rho_{va}}{r_{va}} \quad (2)$$

where $\rho_{va}$ and $\rho_{vs}'$ are water vapor concentrations in the air and at the condensing surface, and $r_{va}$ is the boundary layer resistance of the plate for vapor.

For small temperature depressions below the dew point, the difference in water vapor concentration between the air and the surface is approximately equal to the slope of the saturation vapor concentration function, s, times the temperature depression, so $$E = \frac{s(T_d - T_s)}{r_{va}} \quad (3)$$

If the mirror cools at a rate, a (C/s), then $T_s = T_d - at$, where t is the time since the surface temperature equaled the dew point temperature, and $T_d$ is the dew point temperature and $T_s$ is the temperature of the mirror surface. Substituting this into equation 3 gives $$E = \frac{sat}{r_{va}} \quad (4)$$

Equation 4 can be substituted into equation 1 and the integration performed to obtain $$W = \frac{sat^2}{2r_{va}} \quad (5)$$

The error in the dew point measurement is $T_d - T_s = at$. Making this substitution into equation 5, and solving for the error gives $$\text{error} = T_d - T_s = \sqrt{\frac{2r_{va}aW}{s}} \quad (6)$$

Table 1 (below) shows the error at various dew point temperatures, assuming that 0.1 g/m² of water is required on the surface to register dew formation, the cooling rate is 0.1° C./s, and the boundary layer resistance is 20 s/m.

TABLE 1

Errors in Dew Point Measurements From Undercooling

| Temp (C) | e(kPa) | s(kPa/C) | $r_{va}$ (g/m3) | s(g/m3/C) | error (C) |
|---|---|---|---|---|---|
| −20 | 0.125335 | 0.010826 | 1.072211 | 0.092611 | 2.07825 |
| −10 | 0.286385 | 0.022641 | 2.356869 | 0.186327 | 1.465185 |
| 0 | 0.611 | 0.044378 | 4.844311 | 0.351849 | 1.066232 |
| 10 | 1.227176 | 0.08217 | 9.386101 | 0.628481 | 0.797781 |
| 20 | 2.336479 | 0.144688 | 17.26114 | 1.068905 | 0.611731 |
| 30 | 4.242051 | 0.24366 | 30.30527 | 1.74071 | 0.479366 |

The errors are clearly too large for precise measurements. Many traditional designs have tried to overcome this error by reducing the rate of cooling near the dew point, either by controlling the surface at the dew point, or by cycling the mirror temperature near the dew point at successively lower rates. Such methods are slow to reach the final dew point temperature, and still have some error because of variability of the boundary layer resistance from application to application. Thus, there is a need to compensate for errors in dew point measurements resulting from overcooling and overheating in measuring dew point temperatures.

Another known technique for measuring dew point temperature involves the use of a chilled-mirror sensor inside a chamber where air is circulated to pass by the sensor. Again, a food sample must be placed in an enclosed space, and the sample and the water vapor in the air surrounding the sample must come to equilibrium before the chilled-mirror sensor will accurately measure the dew point. A primary benefit has been observed in measurement systems where air is circulated in the measurement chamber. Circulation of air speeds up the period of time required for equilibrium. Use of a fan, for example, to circulate the air has reduced the time to establish equilibrium to less than five minutes.

In spite of the speed at which chilled-mirror sensors using a fan for circulating air allow equilibrium to take place, boundary layer resistance in known prior devices has caused air circulation to flow far above the chilled mirror, thereby preventing enhanced accuracy of measurements, increased speed in measuring the dew point temperatures, and time required for equilibrium.

Accordingly, there is a need to provide a method of reducing the boundary layer effects associated with traditional chilled-mirror sensors to speed up equilibrium, improve precision, and increase the speed with which dew point temperature measurements can be made.

There is also a need to provide a controlled environment for measuring the relative humidity of air, either ambient air surrounding the measuring system or a sample of air in a chamber that has reached equilibrium with a product sample, to reduce the problems associated with adsorption in high humidity applications.

Still another need exists to provide a method of correcting traditional errors associated with measuring dew point temperatures using chilled-mirror sensors.

OBJECTS AND SUMMARY OF THE INVENTION

It is an object of the invention to provide a relative humidity measuring apparatus that speeds up the period of time by which equilibrium is reached in a chamber where an air sample is to be measured.

Another object of the invention is to provide a relative humidity measuring apparatus that speeds up the period of time by which equilibrium is reached in a chamber where a product sample has been introduced and the relative humidity of an air sample within the chamber is to be measured.

Still another object of the invention is to provide a relative humidity measuring apparatus that increases the accuracy of dew point temperature measurements taken in a sealed chamber.

Another object of the invention is to provide a relative humidity measuring apparatus that speeds up the time required for dew point temperature measurements in chilled-mirror sensors.

Another object of the invention is to provide a device for accurately and quickly determining the relative humidity of ambient air.

Still another object of the present invention is to provide a relative humidity measuring apparatus that controls the temperature of the chamber at a temperature higher than the temperature of the sample to control adsorption within the chamber in high humidity or extreme precision applications and thereby speed up the period of time required for reaching equilibrium within the chamber.

Another object of the invention is to provide a relative humidity measuring device that utilizes a temperature control device to speed up the period of time required for reaching equilibrium in systems using capacitive or resistive sensors used to measure equilibrium relative humidity.

Another object of the invention is to provide a relative humidity measuring device that utilizes a sample temperature measuring device to speed up the period of time required for reaching equilibrium and/or to increase accuracy of measurements in systems using capacitive or resistive sensors used to measure equilibrium relative humidity.

Another object of the invention is to provide a relative humidity measuring device that utilizes a temperature controld device, such as a heater, to speed up the period of time required for reaching equilibrium and/or to increase accuracy of measurements in systems using capacitive or resistive sensors used to measure equilibrium relative humidity.

Yet another object of the present invention is to provide a method of circulating air in a chamber in which dew point temperature measurements of an air sample are measured so that adverse effects of boundary layer resistance are minimized.

Yet another object of the invention is to provide a method of minimizing the adverse effects of boundary layer resistance in dew point temperature measuring systems to increase the speed with which the actual dew point is calculated.

Still another object of the invention is to provide a method of minimizing the adverse effects of boundary layer resistance in dew point temperature measuring systems to decrease interval times between measurements and thereby facilitate the tracking of changes in dew point temperatures.

Yet another object of the invention is to provide a method of minimizing adverse effects of boundary layer resistance in dew point temperature measuring systems to minimize contamination of the condensing surface.

Yet another object of the invention is to maintain high accuracy dew point measurements in applications involving water activity and general measurements of ambient air relative humidity.

Another object of the invention is to provide an air circulation system within a chamber in which water activity of a product sample is measured by determining the dew point temperature within the chamber by forcing air flow directly onto a dew point measurement surface to reduce boundary layer resistance.

Still another object of the invention is to provide an equilibrium relative humidity measuring device wherein an air sample passes through a membrane prior to entering into a chamber in which the equilibrium relative humidity measurement is taken.

Another object of the invention is to provide an equilibrium relative humidity measuring apparatus in which the relative humidity of a sample of air is measured, and in which the temperature of the sample of air is controlled.

The foregoing objects are achieved by a dew point temperature measuring apparatus and method in and by which relative humidity of ambient air or water activity may be measured. The system involves a sealed chamber in which a food product is placed and air is circulated, a sensing device, such as a chilled-mirror sensor, to measure the dew point temperature of air within the chamber, a sensor to measure the temperature of the sample, an air circulation device mounted within the chamber, and a diverter for directing air flow directly onto the sensor to minimize detrimental effects of boundary layer resistance. The dew point temperature measuring system may also be used to determine the dew point temperature of ambient air.

Another embodiment of the invention utilizes a sealed chamber in which a product sample is placed, a sensor such as a chilled-mirror sensor, for measuring the dew point temperature of air within the chamber, a sensor to measure the temperature of the sample inside the chamber, and a fan positioned in the chamber so as to force air within the chamber directly onto the sensor for minimizing the detrimental effects of boundary layer resistance.

Yet another embodiment of the present invention involves a relative humidity measuring system including a temperature control device, such as a heater used in conjunction with the chamber to maintain air within the chamber at a temperature different than the temperature of the sample to control adverse effects of adsorption within the chamber in high humidity or extreme precision applications to speed up the time required for the chamber to reach equilibrium.

Another embodiment of the present invention involves a relative humidity measuring device including a sample temperature measuring device to speed the time required for equilibrium and/or increase accuracy of measurements of the relative humidity measuring device.

Still another embodiment of the present invention involves a relative humidity measuring apparatus, including a membrane, such as Gortex, through which an air sample is directed prior to entering into a chamber in which the relative humidity of the air sample is measured.

Other objects, features, and advantages of the invention will become apparent from the following detailed description of the invention with reference to the accompanying drawings.

BRIEF DESCRIPTION OF THE DRAWINGS

Preferred embodiments of the invention are described below with reference to the accompanying drawings.

DETAILED DESCRIPTION OF THE INVENTION

Figure 1:
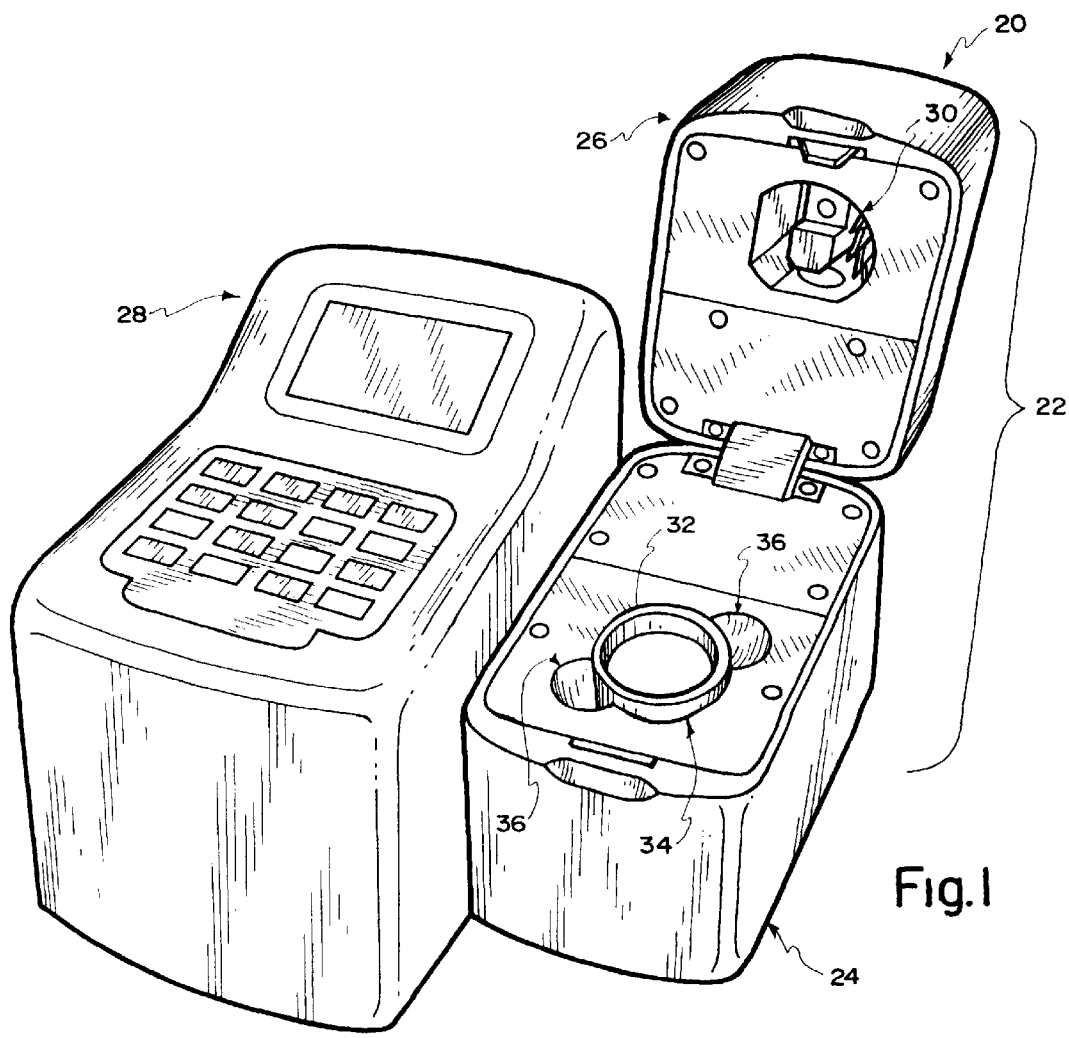
FIG. 1 is an isometric view of a water activity measuring apparatus including a chamber in which water activity of a product sample is measured according to the present invention.

FIG. 1 shows a dew point temperature/water activity measuring apparatus 20 having a housing 22 which includes a base 24 and a cover 26. The housing 22 is operatively connected by means of a circuit board to a data input/output control unit 28 operatively coupled to the housing 22. Data to be input through the control unit may include the sample number, the time at which measuring should begin, and temperature control data. Output data may include temperature measurements, water activity measurements, and other measurements obtained by the apparatus 20.

The water activity measuring device 20 may be used to determine the water activity of many different product samples, such as food products, plants, soils, and most anything that contains moisture. The device 20 is particularly suitable for measuring water activity of food products. It is to be understood, however, that a version of the device 20 may be used to measure the dew point temperature of any sample of air within its chamber. Water activity of a food product is defined as follows:

$$A_w = \frac{e_a}{e_o(T_s)} \qquad (7)$$

where the $e_a$ is the vapor pressure of air in equilibrium with the sample surface and $e_o(T_s)$ is the saturation vapor pressure $e_o$ at sample surface temperature $T_s$. The vapor pressure of the air is equal to the saturation vapor pressure at dew point temperature (i.e., the temperature at which dew forms on a mirror or other reflective surface). The saturation vapor pressure is closely approximated by the following equation:

$$e_o(T) = a \exp\left(\frac{bT}{T+c}\right) \qquad (8)$$

where a, b, and c are constants and T is the sample surface temperature. Substituting equation 8 into equation 7 gives $$A_w = \frac{a \exp\left(\frac{bT_d}{T_d+c}\right)}{a \exp\left(\frac{bT_s}{T_s+c}\right)} = \qquad (9)$$

$$\exp\left(\frac{bT_d}{T_d+c} - \frac{bT_s}{T_s+c}\right) = \exp\left(\frac{bc(T_d-T_s)}{(T_d+c)(T_s+c)}\right)$$

where $T_s$ is the surface temperature and $T_d$ is the dew point temperature in degrees Celsius.

The value of c is 241° C., so small absolute errors in either the surface or the dew point temperature measurement have almost no effect on the water activity. For accurate water activity measuring, therefore, errors in measuring the difference between surface temperature and dew point temperature are the most critical. To be accurate, the difference between these two temperatures should be zero when the sample and mirror temperatures are equal.

Since the error in water activity $A_w$ is almost entirely due to error in $\Delta T=(T_d-T_s)$ we can easily determine the sensitivity of a water activity measurement $A_w$ to this type of error by differentiating equation 9 with respect to $\Delta T$. This gives $$\frac{dA_w}{d\Delta T} = \exp\left(\frac{bc\Delta T}{(T_s+c)(T_d+c)}\right) \frac{bc}{(t_s+c)(T_d+c)} = \frac{A_w bc}{(T_s+c)(T_d+c)} \qquad (10)$$

This equation indicates that the temperature errors are largest at high water activity and decrease approximately linearly as water activity decreases. Since the denominator increases somewhat with temperature, errors should be less important at high measurement temperature as compared to low measurement temperature. The value of b is 17.5 $C^{-1}$. If $T_s=T_d=20°$ C. and $A_w=1$ then $dA_w/d\Delta T=0.06°$ C. Therefore, to meet an accuracy specification of ±0.003 in water activity $A_w$ (for precision water activity measurements), a temperature difference accurate to 0.003/0.06=0.05° C. is needed. Chromel-constantan thermocouples having an output of 60 $\mu$v/C have been used, and the thermopile output is similar so the required voltage resolution is 3 $\mu$v.

The present invention provides still further advances with respect to accuracy of water activity measurements of product samples, as well as dew point measurements for atmospheric air. Among other things, the improvements relate to controlling the flow of air within the measurement chamber to minimize adverse effects of boundary layer resistance, providing a temperature control device, such as either a heater or a cooler for the sample product, for the chamber to maintain the temperature of all internal surfaces slightly higher than the temperature of the sample product when measuring water activity involving product samples having a high humidity. It has been determined that creating a non-isothermal chamber, preferably at 1° C. temperature difference between internal chamber surfaces and the surface temperature of the product sample, results in approximately 6% humidity difference. The result of the chamber being even 0.5° C. warmer than the sample is that the humidity in the chamber is about 3% lower than the sample humidity. If pure water is put in the chamber (with water being at 100% humidity), the chamber reaches a humidity of 97%, well below the point at which significant adsorption of water vapor occurs on the chamber surfaces. The result is that the time required to reach equilibrium within the chamber is drastically reduced.

Referring again to FIG. 1, the housing 22 defines a chamber 30 in which water activity of a product sample (not shown) to be held by a container 32 is measured. The container 32 seals against the bottom surface of cover 26 such that the inside of container 32 (with the product sample held inside) forms part of the resulting sealed chamber. The container 32 rests within a corresponding recessed area 34 formed in the base portion 24 of the housing 22. Opposed dished-out areas 36 are provided to enable the container 32 to be readily installed into and removed from the recessed area 34 formed in the base 24. A bias member (not shown) is positioned between the bottom of recessed area 34 and container 32 to bias the container 32 upwardly such that when the cover 26 is secured in place over the base 24, the container 32 is biasedly held against the bottom surface of cover 26 to seal the chamber 30. Precision water activity measurements require the chamber to be completely sealed.

Figure 3:
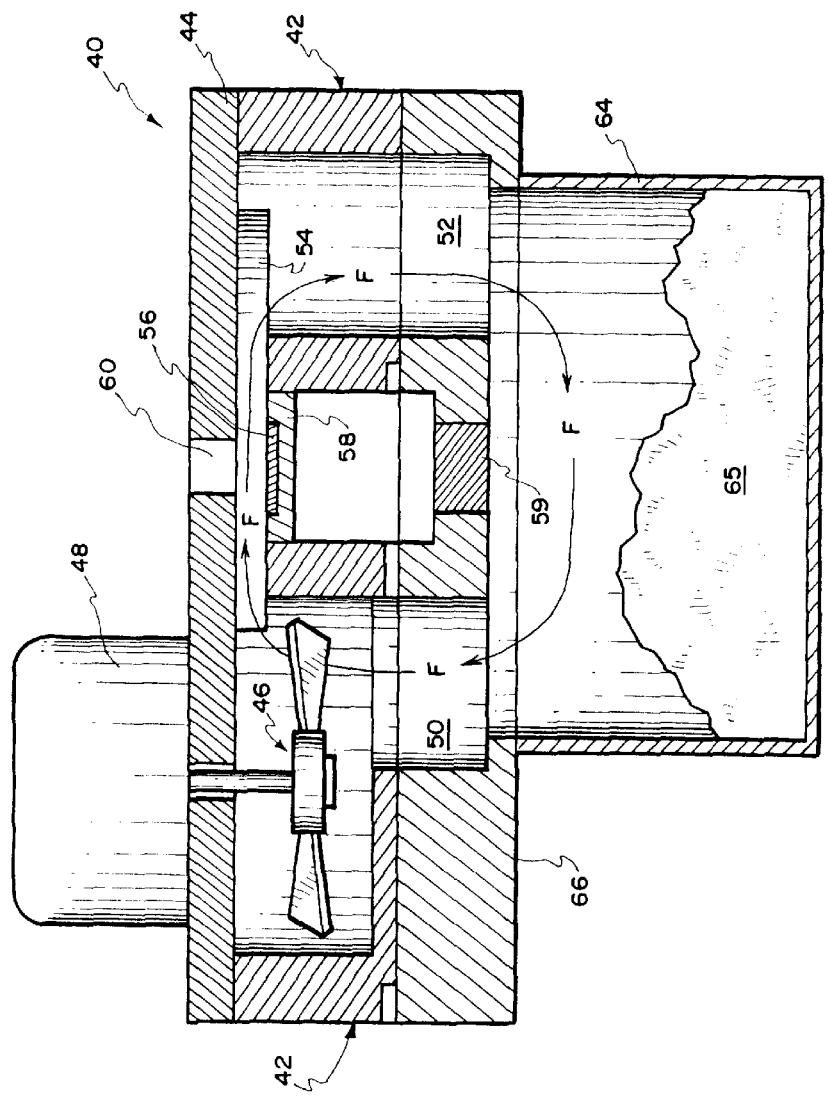
FIG. 3 is a sectional front elevation view of the block and chamber of FIG. 2, with the lid sealed in position against the block to form the chamber and a container with a product sample sealing the bottom of the chamber.
Figure 2:
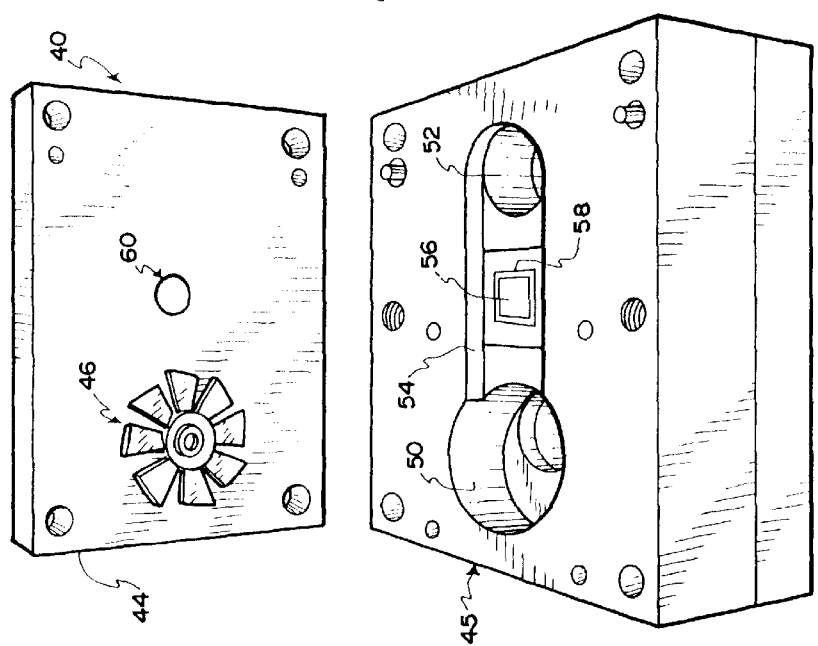
FIG. 2 is a front perspective view of a prior art block in which a chamber is formed for measuring water activity, with the lid of the chamber shown in a raised position.

FIGS. 2 and 3 show a prior art water activity measuring apparatus 40. The measuring apparatus 40 includes a base 42 and a cover 44. A fan 46 is mounted to the cover. A fan motor 48 is attached to the cover 44 which causes the fan to rotate and create an air flow F (as shown in the arrow in FIG. 3) within the chamber. Such an air flow has been shown to speed up the period of time for the chamber to reach equilibrium.

The chamber is generally defined by a first opening 50 formed in the base (in which fan 46 is inserted) a second passageway 52, and an interconnecting channel 54 fluidly connecting passageway 50 and passageway 52. A mirror 56 (and temperature sensor associated therewith) mounted on top of a thermo-electric cooler 58, a so-called Peltier cooler, is positioned within the interconnecting channel 54. The Peltier cooler 58 is utilized to cool the mirror until dew forms on the mirror and subsequently to heat the mirror until dew disappears to determine an actual dew point temperature (assumed to be the temperature at which liquid water and water vapor are at equilibrium) to measure the vapor pressure of air within the chamber. The presence of dew on the mirror is detected by an optical sensor 60 coupled to the cover 44 of the water activity measuring apparatus 40.

A container 64 is secured in position to sealingly engage a bottom surface 66 of the base 42. Thus, a sealed chamber is created. In the application of the present technology to dew point temperature measurements of atmospheric humidity, however, no sealed chamber is necessary. Rather, a type of flow-through system may be utilized.

A product sample 65, such as a food sample, is placed inside the container 64 when it is desired to measure the water activity of the product sample. A sensor 59, such as a thermopile sensor, is secured to the base 42 so as to be directly over the product sample 65. The sensor 59 detects the surface temperature of the product sample 65.

The prior art water activity measuring device shown in FIGS. 2 and 3 would begin its measuring procedure as soon as the container 64, including the product sample 65, was sealed against the lower surface 66 of the base 42. The fan 46 would then be activated to create an air flow F within the chamber, as shown. As mentioned, circulation of air within the chamber has been found to increase the speed with which the chamber reaches equilibrium. Equilibrium within the chamber was determined by taking a series of water activity measurements at approximately one minute intervals. As soon as two successive readings resulted in measurements that differed less than one-tenth of a percent, it was assumed that equilibrium had been reached.

An aspect of the present invention involves utilization of an extrapolation method to predict the actual water activity measurement based upon a few initial readings. This would speed up greatly the period of time required to make a water activity measurement. The extrapolation procedure would match the product sample being measured with known characteristics to predict accurately the relative humidity or water activity for the product sample, even though only a limited number of measurements have been taken. This will speed up the time required for accurate relative humidity or water activity for a given sample of air being tested.

Figure 6:
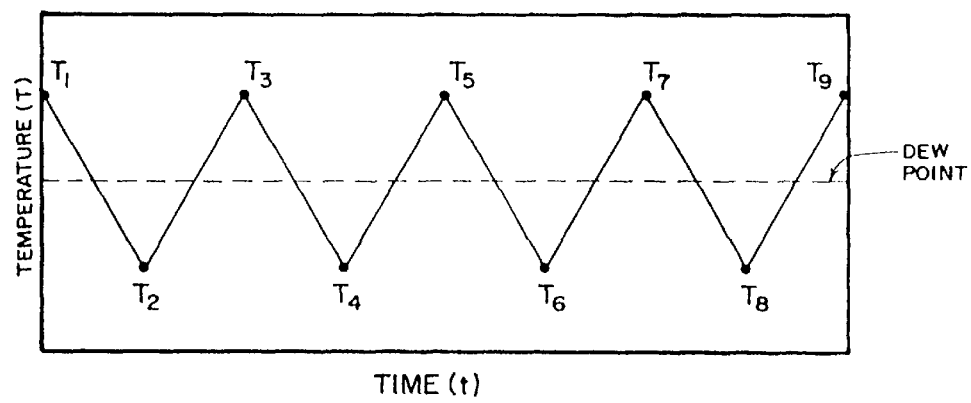
FIG. 6 is a diagrammatic view of a graph showing a plot of temperature of a chilled mirror vs. time as a final dew point measurement of a product sample is calculated according to the present invention.

One of the problems with respect to the prior art devices such as those shown in FIGS. 2 and 3 is that boundary layer resistance causes air to flow above the surface of the mirror 56, which adversely affects measurement of dew point temperatures. Primary draw backs with respect to these prior methods are that they are slow to reach the final dew point temperature, and some errors inevitably result because of the variability in the boundary layer resistance from application to application. Typically, boundary layer resistance is not controlled and, accordingly, will vary considerably between applications. The device shown in FIGS. 2 and 3 cools the surface of the mirror until dew forms, measures the surface temperature, then heats the surface until the dew just disappears, and takes a second temperature reading. This relationship is shown in the graph of FIG. 6, which shows a graph of temperature measurements of a chilled-mirror sensor against time. To begin, the Peltier cooler reduces the surface temperature of the mirror from $T_1$ to a lower temperature $T_2$. The reduction in temperature from $T_1$ to $T_2$ may be more rapid than subsequent temperature changes. Once the temperature of the mirror reaches $T_2$, dew has formed on the surface of the mirror. At this time, the rate of cooling is reversed, which warms the surface of the mirror until the temperature reaches $T_3$, at which time all dew has evaporated from the mirror. Temperatures $T_2$ and $T_3$ are averaged (as are subsequent pairs of extremes—$T_4$ and $T_5$, $T_6$ and $T_7$, etc.) to determine the dew point of the air being circulated in the chamber. Temperatures $T_4$, $T_6$, $T_8$ are where dew has formed on the surface of the mirror, and temperatures $T_5$, $T_7$, and $T_9$ are where dew has evaporated from the mirror.

Assuming that boundary layer resistance is the same during cooling and heating in the process shown in FIG. 6, the under cooling when dew forms should be the same as over cooling when dew evaporates (assuming the cooling and heating rates are equal). The average of these two extreme temperature differences should therefore be the correct dew point. Again, a major disadvantage with respect to this method relates to the amount of time taken for a measurement and the requirement to slowly change the temperature of the mirror surface through the dew point temperature. If measurements are made too far apart in time, not enough data will be obtained to monitor adequately changes in the dew point. If the dew point temperature changes while the measurement is being made, errors are introduced because of the asymmetry in heating and cooling which makes it difficult to even track the changing dew point.

Figure 5:
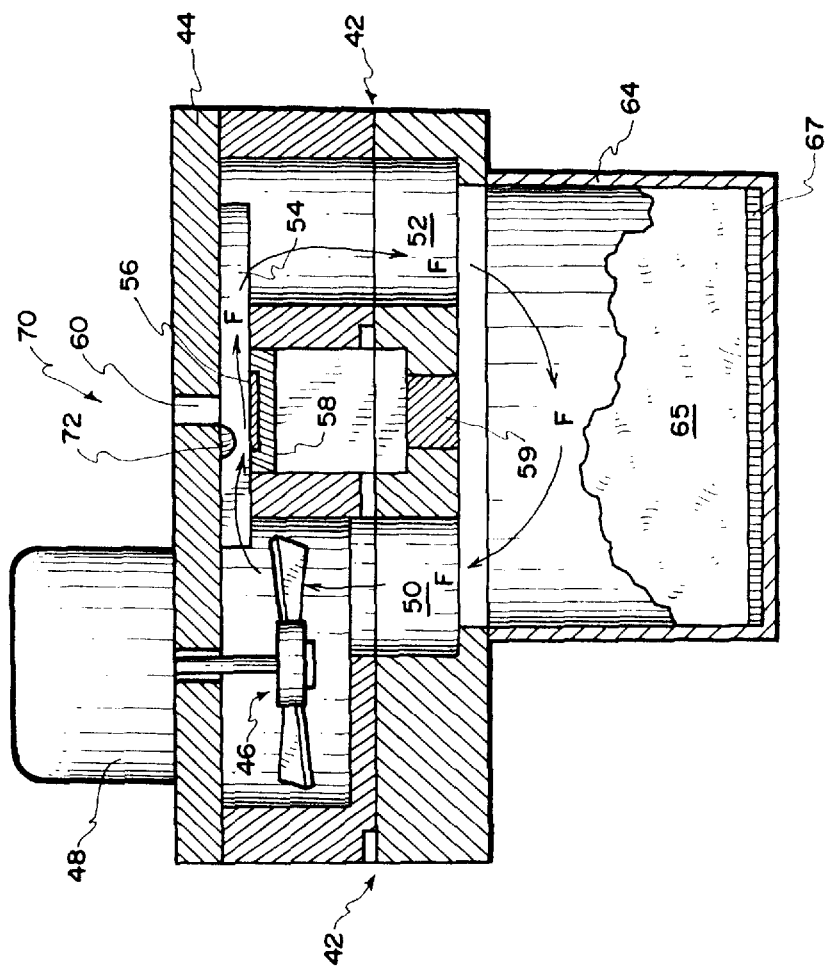
FIG. 5 is a sectional front elevation view of the chamber of FIG. 4.
Figure 4:
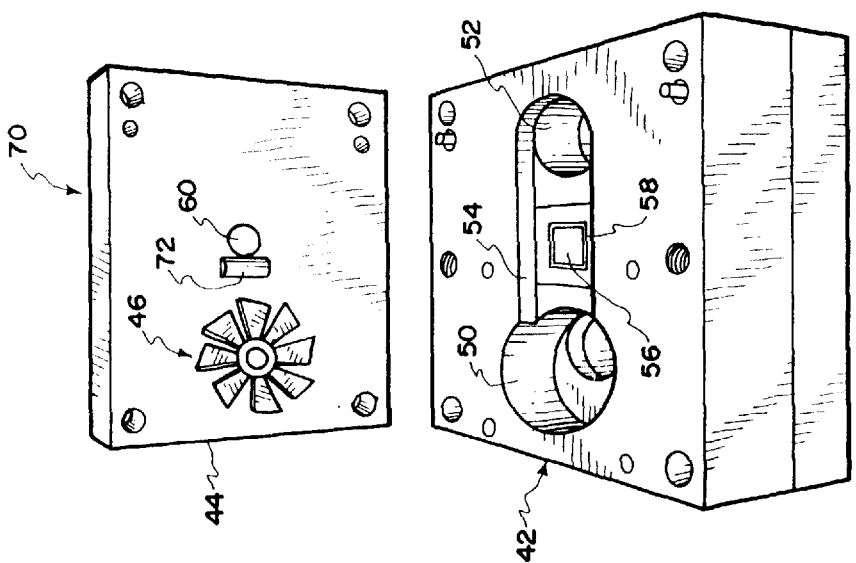
FIG. 4 is a front perspective view of a block in which a chamber is formed for measuring water activity of a product sample, with the lid of the chamber shown in a raised position, and a baffle formed on the top of the chamber to divert air being circulated within the chamber directly onto a sensor within the chamber according to the present invention.

FIGS. 4 and 5 show an embodiment of a dew point temperature measuring apparatus 70 according to the present invention. The apparatus 70 may be used for determining water activity of a product sample, or a slightly modified version may be used to measure relative humidity of atmospheric air. A new method according to the present invention seeks to control the boundary layer resistance of the condensing surface, to monitor conditions existing during cooling and dew formation, and to correct for the error introduced using equation 6 (found in the background of the invention section).

Boundary layer resistance can be computed from $$r_{va} = 283\sqrt{\frac{d}{u}} \tag{11}$$

where d is the width of the surface (m) and u is the velocity of air over the surface (m/s). The method seeks to minimize d and maximize u to minimize the boundary layer resistance and thus minimize the error. The air velocity must be known, and should be constant to give best accuracy.

The advantages of using the inventive method include increased speed with which measurements can be made to determine accurately the dew point temperature. Cooling rates can be high with accuracy also remaining high. In addition, it becomes much easier to track a changing dew point temperature because the higher speed makes it possible to follow changing dew point temperatures.

Furthermore, there is less contamination of the condensing surface because it is wet for shorter periods of time. Breaking up the boundary layer resistance will cause faster condensation and evaporation when the reflective surface is cooled and heated, respectively. Finally, accuracy with respect to all dew point temperature measurement applications will be increased, since boundary layer resistance will be controlled and certain air flow variables, such as air velocity, will be known.

Most of the structural aspects of the embodiment of FIGS. 4 and 5 are similar to those shown in FIGS. 2 and 3, such as a mirror (and integral temperature sensor—not shown) 56 and a Peltier cooler 58, and a thermopile 59 which determines the sample temperature. The primary difference is that a baffle 72 is formed in the cover 44 adjacent the reflectance sensor 60. The baffle 72 serves as a deflector to direct the flow of air F within the chamber downward to directly impinge upon the surface of mirror 56. This flow pattern of air within the chamber creates a greater speed of air flow F across the mirror surface and creates turbulence immediately above the mirror to minimize detrimental effects due to boundary layer resistance traditionally occurring just above the mirror 56. This type of flow diversion will reduce boundary layer resistance and thereby speed up the amount of time required to reach equilibrium in the chamber, improve the accuracy of dew point temperature measurements, and minimize the amount of time required between successive dew point measurements.

Figure 7:
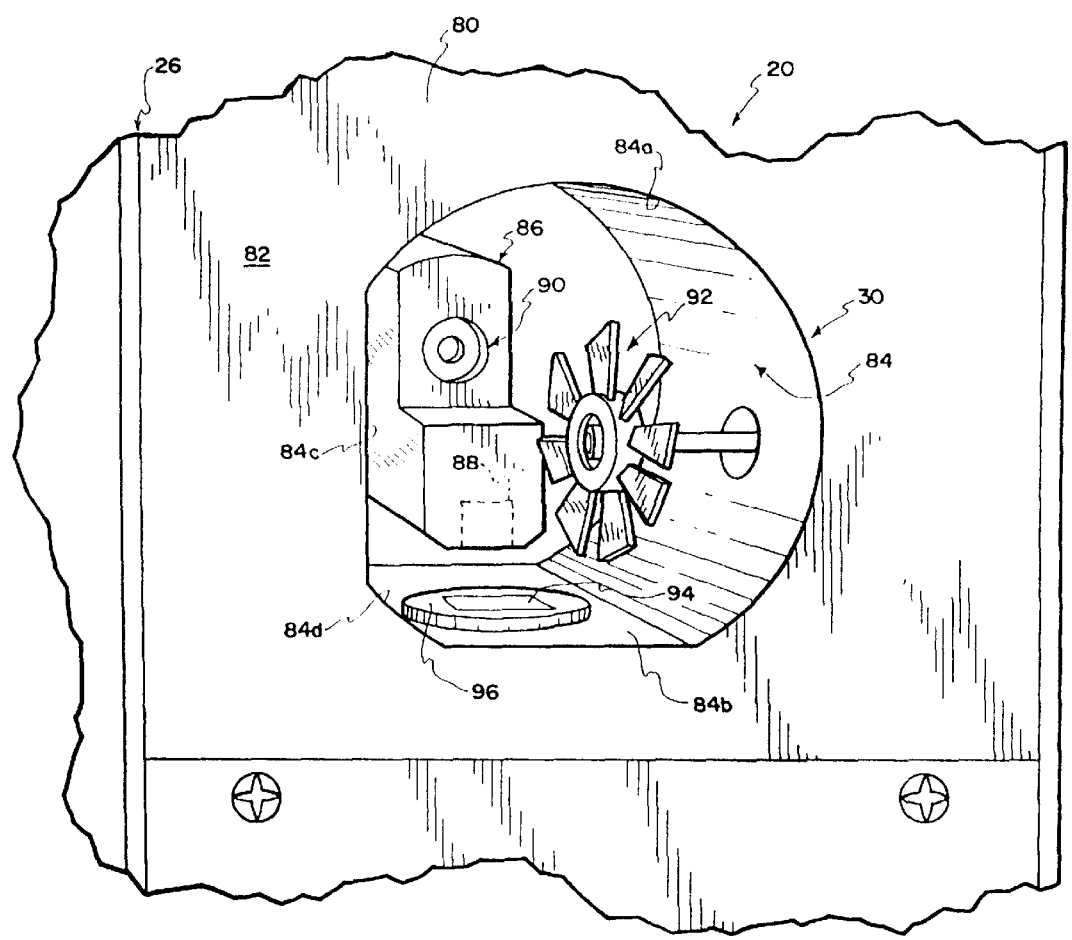
FIG. 7 is an enlarged perspective view of the chamber of FIG. 1 in which water activity of a product sample is measured according to the present invention.
Figure 9:
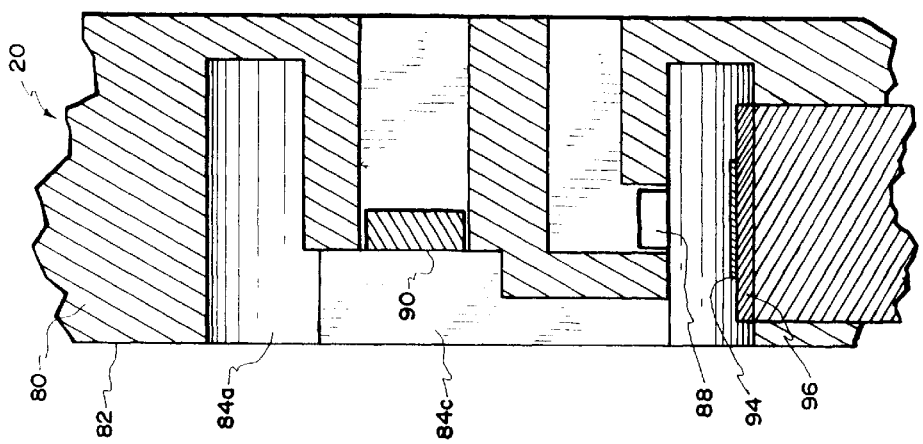
FIG. 9 is a sectional side elevation view, taken along the line 9—9 of FIG. 8, of the chamber according to the present invention.
Figure 8:
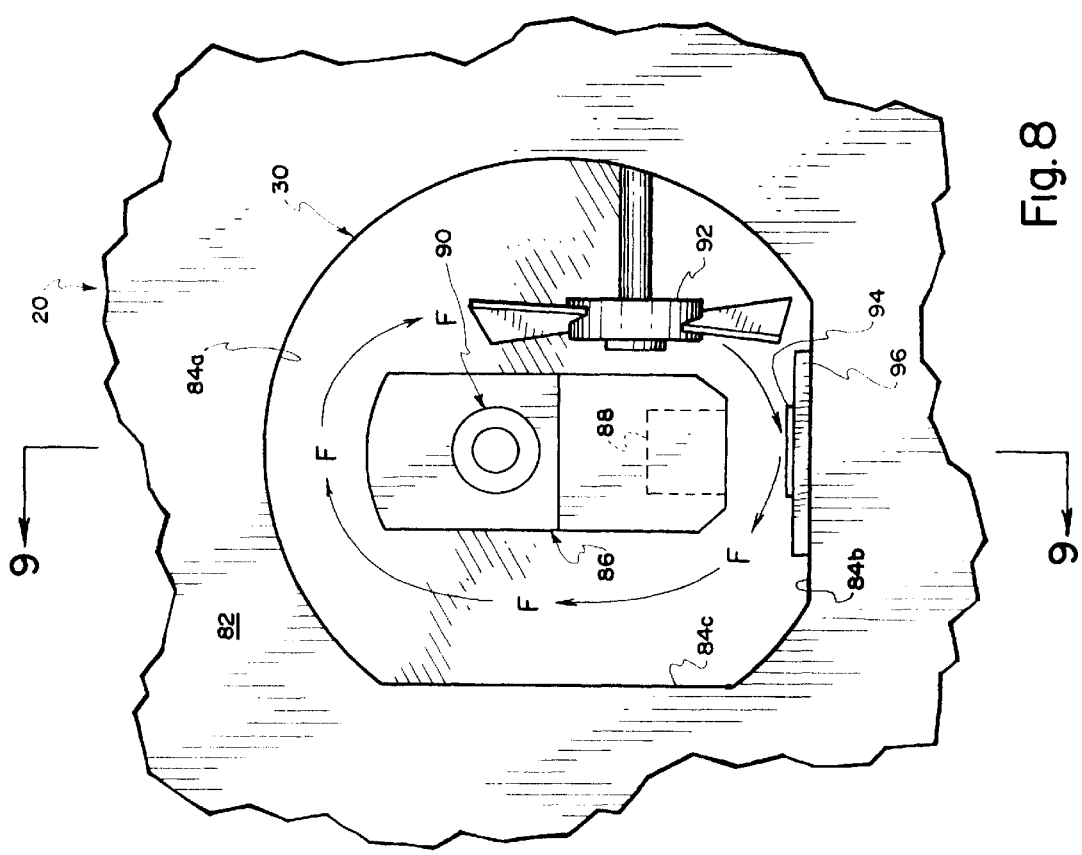
FIG. 8 is a front side elevation view of the chamber of FIG. 7.

FIGS. 7–9 show additional details of the chamber 30 of the embodiment of FIG. 1. As mentioned, the chamber 30 is formed in a cover 26 which articulates to a closed position against the base 24 (FIG. 1) such that the chamber 30 is sealed over the top peripheral edge of container 32. The cover 26 includes a block or housing 80 having a bottom surface 82. A chamber opening 84 is formed in the housing 80. The chamber opening 84 includes a curved edge 84a, a first flat edge 84b, a second flat edge 84c, and an interconnecting edge 84d which joins edges 84b and 84c. The flat edges 84b, 84c, and 84d are primarily intended to reduce air space within the chamber opening 84.

A block 86 is mounted to the cover 26 so as to extend inside the chamber 84. The specific configuration of block 86 contributes to the air space within chamber opening 84, air flow F inside the opening, and the locations where sensors 88 and 90 are preferably mounted. The block 86 includes an optical sensor 88 (shown in hidden lines in FIG. 7) and a thermopile or an infrared temperature sensor 90. A fan 92 is mounted within the chamber 30 to circulate air inside the opening 84, and around the block 86 and product sample held within container 32 (FIG. 1). The chamber 84 includes the inside of the container 32 when surface 82 engages the rim of the container.

Positioned immediately below the optical sensor 88 is a mirror 94 (including a temperature sensor—not shown—for sensing the mirror temperature), which is mounted, in turn, on top of a thermoelectric cooler 96 (such as a Peltier cooler). Sensor 88 detects the presence or absence of dew on the mirror. Sensor 90 detects the surface temperature of the product sample.

As shown in FIG. 8, the fan 92 rotates in such a way that a flow of air F is forced toward and directly impinges upon the surface of mirror 94 to minimize detrimental effects of boundary layer conditions. The air flow rate (which may be varied by changing the rotational speed of the fan) may be monitored, so that boundary layer resistance can be quantitatively understood and controlled to reduce boundary layer resistance and enable corrections for boundary layer effect errors (see discussion above).

Figure 10:
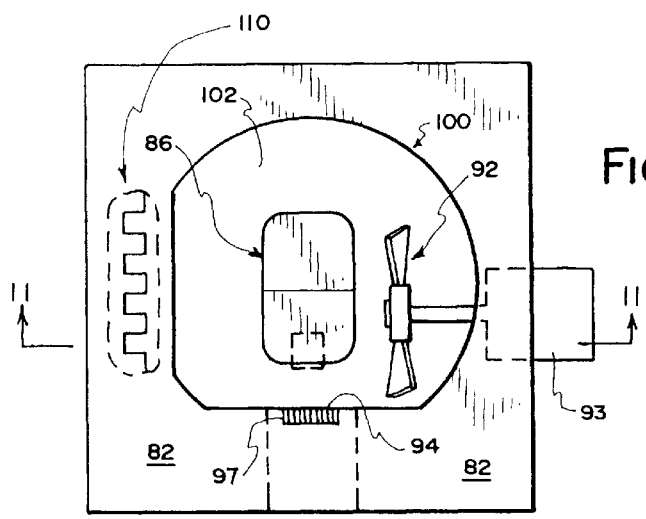
FIG. 10 is a sectional front elevation view of an alternative embodiment of a dew point measuring apparatus to measure atmospheric humidity.
Figure 11:
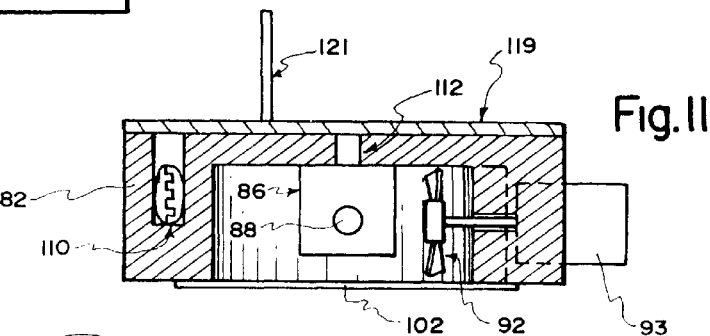
FIG. 11 is a bottom sectional view of the alternative embodiment of FIG. 10.

FIGS. 10 and 11 show another alternative embodiment of the present invention for measuring relative humidity of ambient air. A chamber 100 formed in a housing is shown, which is similar in configuration (thus similar elements are numbered the same) to the chamber shown in FIGS. 7–9. The opening of chamber 100 is covered by a vapor permeable membrane 102 which serves as a barrier between the chamber 100 and the ambient air. The vapor permeable membrane may be made of a material such as Gortex, which allows vapor to pass through the membrane, but prevents liquid and other debris from passing through the apertures. This particular embodiment is intended to be used in measuring atmospheric humidity of, for example, a room or other location, where the ambient air being measured may include debris and other non-vapor substances that may otherwise reduce the accuracy of humidity measurements.

The embodiment of FIGS. 10 and 11 also shows a heater 110 which is mounted within the housing 82 which defines the chamber 100. It is to be understood that a heater, similar to the heater 110 in FIGS. 10–11, may be utilized in any of the embodiments of the present invention to warm the temperature of internal surfaces of a chamber (such as chamber 50 in FIG. 5) to create a temperature differential relative to ambient air. An atmospheric temperature sensor 121 is coupled to a pc board 119, which is in turn operatively coupled to the device. The embodiment shown in FIGS. 10 and 11 should be used in high humidity application or applications where high precision accuracy is required.

With respect to the embodiment shown in FIGS. 4 and 5, or the embodiment shown in FIGS. 8 and 9, a temperature differential may also be created within a sealed chamber to create a non-isothermic chamber. This can be accomplished by placing a heater in the respective blocks or housings, and warming internal chamber surfaces. Alternatively, as shown in FIG. 5, a Peltier cooler 67 may be provided underneath the sample 65 to cool the sample to create a temperature differential between the sample and the air being circulated in the chamber.

Figure 12:
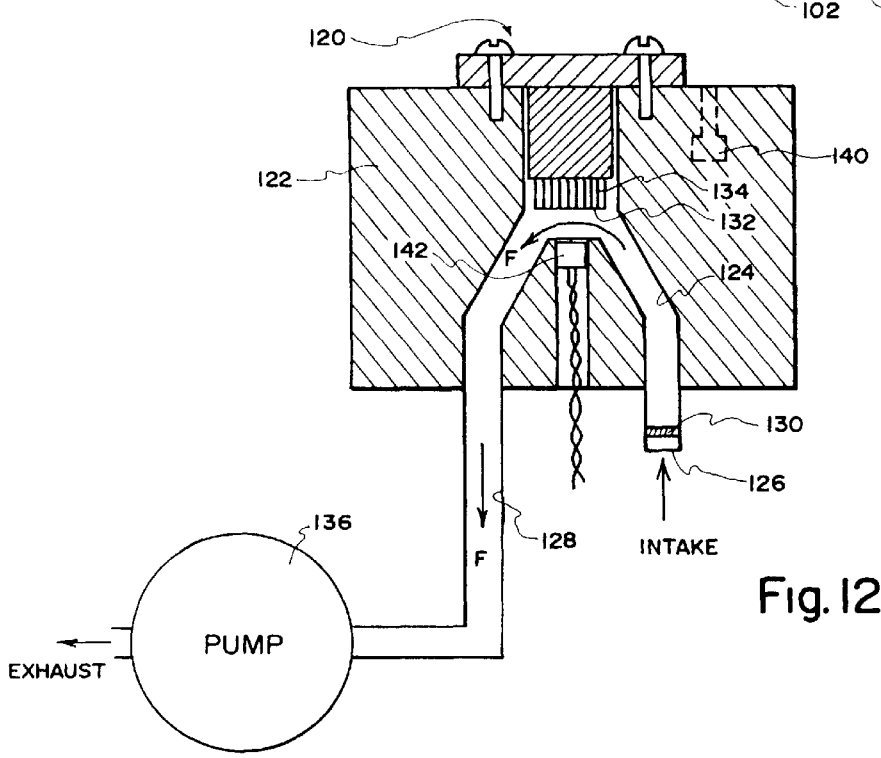
FIG. 12 is a top sectional view of another alternative embodiment of a dew point measuring apparatus to measure atmospheric humidity.

FIG. 12 shows still another embodiment of the present invention, which comprises a device 120 for measuring the relative humidity of ambient air. A housing or block of material 122 is provided in which a passageway 124 having an inlet 126 and an outlet 128 are provided. A filter 130 may be mounted within the intake to remove impurities from the ambient air being measured. Air is directed through passageway 124 such that it impinges directly upon a mirror 132 mounted on top of a cooler 134 (such as a Peltier cooler). Air is drawn through passageway 124 by means of a pump 136 which is operatively coupled to the passageway 124. A temperature sensor 140 is provided to determine temperature of the block which will enable accurate measurements of the relative humidity of ambient air (i.e., air surrounding the measuring device, such as air in a particular room or location). The humidity is measured using the above-mentioned techniques for obtaining accurate dew point temperature measurements. It is to be understood that the mirror 132 can be mounted within the passageway 124 in such a manner that air flowing through passageway 124 directly impinges upon the mirror, to minimize adverse effects of boundary layer resistance, thereby speeding up measurements of relative humidity. An optical sensor 142 is provided within the block for detecting the presence of dew or moisture on the mirror 132.

Figure 13:
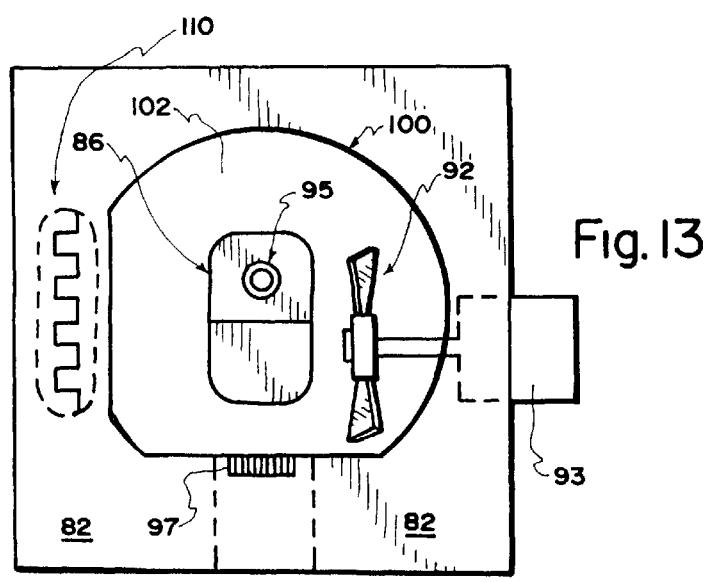
FIG. 13 is a sectional front elevation view of still another alternative embodiment of the present invention involving a dew point measuring apparatus including a resistive or capacitive sensor for measuring the dew point temperature, and a sample temperature measuring device.

FIG. 13 discloses yet another alternative embodiment of the invention. Some elements shown in FIG. 13 are similar to certain elements shown in FIGS. 10 and 11, and therefore have similar reference numerals. The embodiment of FIG.

13 includes a sensor 95 (such as a thermopile) for determining the temperature of a product sample to be measured. In contrast to the embodiment of FIG. 10, the FIG. 13 embodiment is preferably utilized in connection with measuring relative humidity of a sample of air withing a chamber 100 in which a product sample is also included. Another type of dew point temperature sensor 97, such as a capacitive or resistive sensor, is positioned within the chamber to determine the dew point temperature of the sample of air when in equilibrium with the product sample. Such sensors determine the humidity based on the change in either resistance or capacitance. In the embodiment of FIG. 13, the heater and/or the fan may be used to speed up the time required to reach equilibrium and to enhance the accuracy of dew point measurements.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications with the proper scope of the appended claims appropriately interpreted in accordance with the doctrine of equivalents.

What is claimed is:

1. A dew point temperature measuring apparatus, comprising:
    a housing;
    a chamber formed in the housing, the chamber being sized to hold a sample of air for measuring a dew point temperature of the sample of air;
    an air circulating device to move the sample of air at a velocity and in a direction through the chamber;
    a dew point sensor positioned inside chamber to measure the dew point temperature of the sample of air, the dew point sensor being positioned within the chamber such that the sample of air moving through the chamber impinges directly upon the dew point sensor, the velocity and the direction of the air flow being controlled to maintain a constant boundary layer resistance and to enhance a rate of condensation upon the dew point sensor.

2. A dew point temperature measuring apparatus according to claim 1, further comprising a baffle positioned within the chamber to cause the sample of air moving through the chamber to directly impinge upon the dew point sensor to minimize adverse effects of boundary layer resistance.

3. A dew point temperature measuring apparatus according to claim 1 wherein the air circulating device forces the sample of air directly upon the dew point sensor to minimize adverse effects of boundary layer resistance.

4. A dew point temperature measuring apparatus according to claim 1 wherein the air circulating device comprises an air pump operatively coupled to the chamber to force the sample of air to flow through the chamber.

5. A dew point temperature measuring apparatus according to claim 1 wherein the air circulating device comprises an air pump operatively coupled to the chamber to force the sample of air to flow through the chamber, and wherein the sample of air comprises ambient air.

6. A dew point temperature measuring apparatus according to claim 1 wherein the sample of air comprises air within the chamber in equilibrium with a product sample also within the chamber.

7. A dew point temperature measuring apparatus according to claim 1 wherein the sensor is a chilled-mirror sensor including a mirror having a top surface, and wherein the airflow within the chamber impinges directly on the top surface of the mirror.

8. A dew point temperature measuring apparatus according to claim 1 wherein the sensor is a chilled-mirror sensor including a mirror having a top surface and an optical sensor for detecting the presence of dew on the top surface of the mirror, and wherein the airflow within the chamber impinges directly on the top surface of the mirror.

9. A dew point temperature measuring apparatus according to claim 1, further comprising a membrane through which the sample of air passes prior to entering into the chamber.

10. A method of measuring a dew point temperature of a sample of air, comprising the steps of:
    providing a housing having a chamber formed therein;
    causing a sample of air to flow at a velocity and in a direction within the chamber;
    providing a dew point sensor to determine the dew point temperature of the sample of air within the chamber;
    forcing the sample of air within the chamber to impinge directly onto the dew point sensor;
    controlling the velocity and the direction of the air flow to maintain a constant boundary layer resistance and to enhance a rate of condensation upon the dew point sensor;
    sensing the dew point temperature of the sample of air within the chamber.

11. The method of claim 10, further comprising the steps of:
    placing a product sample within the chamber;
    allowing the sample of air within the chamber to reach equilibrium with the product sample;
    sensing the dew point temperature of the sample of air in equilibrium with the product sample.

12. The method of claim 10, further comprising the steps of:
    placing a product sample within the chamber;
    providing a heater in the housing;
    heating the housing to increase the temperature in the chamber above the temperature of the sample;
    allowing the sample of air within the chamber to reach equilibrium with the product sample;
    sensing the dew point temperature of the sample of air in equilibrium with the product sample.

13. The method of claim 10, further comprising the steps of:
    placing a product sample within the chamber;
    providing a heater in the housing;
    heating the housing to increase the temperature in the chamber 0.5 degrees C. above the temperature of the sample;
    allowing the sample of air within the chamber to reach equilibrium with the product sample;
    sensing the dew point temperature of the sample of air in equilibrium with the product sample.

14. The method of claim 10, further comprising the steps of:
    placing a product sample within the chamber;
    providing a cooler adjacent the product sample;
    cooling the product sample to lower the temperature of the product sample below the temperature of the chamber;

allowing the sample of air within the chamber to reach equilibrium with the product sample;

sensing the dew point temperature of the sample of air in equilibrium with the product sample.

15. The method of claim 10, further comprising the steps of:

placing a product sample within the chamber;

providing a cooler adjacent the product sample;

cooling the product sample to lower the temperature of the product sample 0.5 degrees C. below the temperature of the chamber;

allowing the sample of air within the chamber to reach equilibrium with the product sample;

sensing the dew point temperature of the sample of air in equilibrium with the product sample.

16. The method of claim 10, further comprising the steps of:

placing a product sample within the chamber;

maintaining the temperature of the chamber 0.5 degrees C. above the temperature of the sample.

17. The method of claim 10, further comprising the steps of:

providing a container;

placing a product sample inside the container;

arranging the container to form part of the chamber such that the product sample is held within the chamber;

allowing the sample of air within the chamber to reach equilibrium with the product sample;

sensing the dew point temperature of the sample of air in equilibrium with the product sample.

18. The method of claim 10 wherein the step of forcing the sample of air within the chamber to impinge directly onto the dew point sensor comprises providing a baffle within the chamber, the baffle causing the sample of air to flow directly onto the dew point sensor to minimize the adverse effects of boundary layer resistance associated with the dew point sensor.

19. The method of claim 10 wherein the step of forcing the sample of air within the chamber to impinge directly onto the dew point sensor comprises positioning a fan within the chamber such that the fan forces air directly onto the dew point sensor to minimize the adverse effects of boundary layer resistance associated with the dew point sensor.

20. The method of claim 10 wherein the sample of air flows within the chamber at a flow velocity, and further comprising the step of changing the flow velocity of the sample of air within the chamber to minimize the adverse effects of boundary layer resistance associated with the dew point sensor.

21. The method of claim 10 wherein the sample air is forced through the chamber circulation device by a fan which rotates at a fan speed and wherein the sample of air flows within the chamber at a flow velocity according to the fan speed, and further comprising the step of changing the fan speed to change the flow velocity of the sample of air within the chamber to minimize the adverse effects of boundary layer resistance associated with the dew point sensor.

22. The method of claim 10 wherein the sample of air is directed through a vapor permeable membrane prior to entering the chamber.

23. An apparatus for measuring the relative humidity of a sample of air to calculate the dew point temperature, comprising:

a chamber configured to hold a sample of air taken from an ambient air environment, the sample of air entering the chamber at an ambient air temperature;

a temperature control device operatively coupled to the chamber to control the temperature of the sample of air within the chamber;

a sensor operatively coupled to the chamber to sense the relative humidity of the sample of air within the chamber so that the dew point temperature can be calculated.

24. An apparatus for measuring the relative humidity of a sample of air to calculate the dew point temperature according to claim 23 wherein the chamber is configured to hold a product sample, and wherein the temperature control device maintains the sample of air at a temperature that differs from the product sample.

25. An apparatus for measuring the relative humidity of a sample of air to calculate the dew point temperature according to claim 23 wherein the temperature control device maintains the sample of air at a temperature that differs from the ambient air temperature.

26. An apparatus for measuring the relative humidity of a sample of air to calculate the dew point temperature according to claim 23, further comprising a membrane coupled to the chamber such that the sample of air is directed through the membrane prior to entering into the chamber.

27. An apparatus for measuring the relative humidity of a sample of air to calculate the dew point temperature according to claim 23, further comprising a vapor permeable membrane coupled to the chamber such that he sample of air is directed through the vapor permeable membrane prior to entering into the chamber.

28. An apparatus for measuring the relative humidity of a sample of air to calculate the dew point temperature according to claim 23 wherein the temperature control device comprises a heater and a temperature sensor, the heater maintaining the sample of air at a higher temperature than ambient air.

29. An apparatus for measuring the relative humidity of a sample of air to calculate the dew point temperature according to claim 23 wherein the chamber is configured to hold a product sample having a product sample temperature, and wherein the temperature control device maintains the sample of air at a temperature above the product sample temperature.

30. An apparatus for measuring the relative humidity of a sample of air to calculate the dew point temperature according to claim 23 wherein the chamber is configured to hold a product sample having a product sample temperature, and wherein the temperature control device maintains the sample of air at a temperature 0.5 degrees C. above the product sample temperature.

31. An apparatus for measuring the relative humidity of a sample of air to calculate the dew point temperature according to claim 23 wherein the sensor is a dew point temperature sensor.

32. A method of measuring relative humidity of a sample of air to determine the dew point temperature, comprising the steps of:

providing a chamber;

introducing a sample of air into the chamber, the sample of having a particular air temperature upon entering into the chamber;

changing the temperature of the sample of air after the sample of air has been introduced into the chamber;

measuring the humidity of the sample of air to determine the dew point temperature.

33. A method of measuring relative humidity of a sample of air to determine the dew point temperature, comprising the steps of:

providing a chamber;

introducing a sample of air into the chamber, the sample of having a particular air temperature upon entering into the chamber;

introducing a product sample into the chamber, the product sample having a product sample temperature;

controlling the temperature of the sample of air so that the temperature of the sample of air is higher than the product sample temperature;

measuring the humidity of the sample of air to determine the dew point temperature.

34. A dew point temperature measuring apparatus, comprising:

a housing;

a chamber formed in the housing, the chamber being sized to hold a sample of air for measuring a dew point temperature of the sample of air;

an air circulating device to move the sample of air at a velocity and a direction through the chamber;

a surface positioned inside chamber, the surface having a temperature, the surface being selectively cooled at a rate causing the surface temperature to decrease with time, a dew formation detector to sense the formation of dew on the surface, a temperature detector to sense the temperature of the surface, the surface being positioned within the chamber such that the sample of air moving through the chamber impinges directly upon the surface, the velocity and direction of the air flow being controlled to maintain a constant boundary layer resistance and to produce a rapid, repeatable transition from a surface free of dew to a dew-covered surface.

35. A method of measuring a dew point temperature of a sample of air, comprising the steps of:

providing a housing having a chamber formed therein;

causing a sample of air to flow at a velocity and in a direction within the chamber;

providing a surface within the chamber;

cooling the surface from a temperature above the dew point temperature to a temperature below the dew point temperature;

providing a dew formation sensor;

utilizing the dew formation sensor to detect the formation of dew on the surface;

providing a temperature sensor;

utilizing the temperature sensor to measure the temperature of the surface instantaneously upon formation of dew on the surface;

forcing the sample of air within the chamber to impinge directly onto the surface;

controlling the velocity and direction of the air flow to maintain a constant boundary layer resistance and to achieve a rapid, repeatable change of surface condition as the surface temperature passes the dew point temperature.

* * * * *